(12) United States Patent
Denis et al.

(10) Patent No.: US 6,313,101 B1
(45) Date of Patent: Nov. 6, 2001

(54) DERIVATIVES OF ERYTHROMYCIN, THEIR PREPARATION PROCESS AND THEIR USE AS MEDICAMENTS

(75) Inventors: Alexis Denis; Claude Fromentin, both of Paris; Bertrand Heckmann, Cachan, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/497,651

(22) Filed: Feb. 3, 2000

(30) Foreign Application Priority Data

Feb. 4, 1999 (FR) .................................................. 99 01292

(51) Int. Cl.⁷ .............................. A61K 31/70; C07H 17/08
(52) U.S. Cl. .................................................. 514/29; 536/7.4
(58) Field of Search .................................. 536/7.4; 514/29

(56) References Cited

U.S. PATENT DOCUMENTS 5,747,467 * 5/1998 Agouridas et al. ..................... 514/29

FOREIGN PATENT DOCUMENTS

| 0676409 | 10/1995 | (EP) . |
| 0680967 | 11/1995 | (EP) . |
| 0799833 | 10/1997 | (EP) . |
| 2732023 | 9/1996 | (FR) . |
| 2732684 | 10/1996 | (FR) . |

* cited by examiner

*Primary Examiner*—Elli Peselev
(74) *Attorney, Agent, or Firm*—Bierman, Muserlian and Lucas

(57) ABSTRACT

A compound of the formula

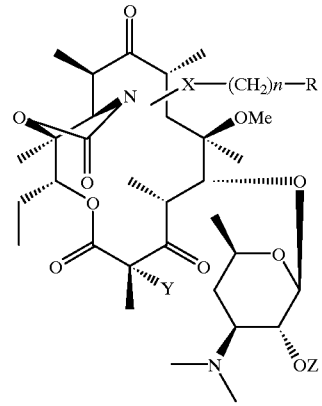

wherein $X=CH_2$ or NH, Y=H or Hal, Z=H or acyl of an organic carboxylic acid of 1 to 6 carbon atoms, R is

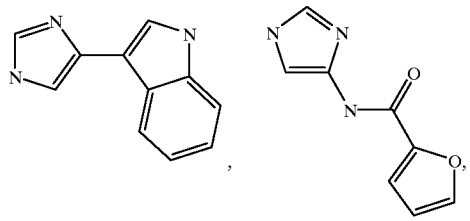

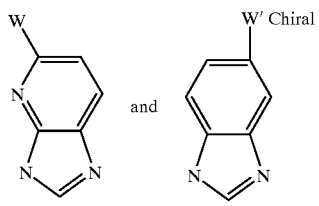

W and W' are individually H, Hal and alkyl of 1 to 8 carbon atoms optionally substituted by at least one halogen having antibiotic properties.

14 Claims, No Drawings

DERIVATIVES OF ERYTHROMYCIN, THEIR PREPARATION PROCESS AND THEIR USE AS MEDICAMENTS

The present invention relates to novel derivatives of erythromycin, their preparation process and their use as medicaments.

A subject of the invention is the compounds of formula

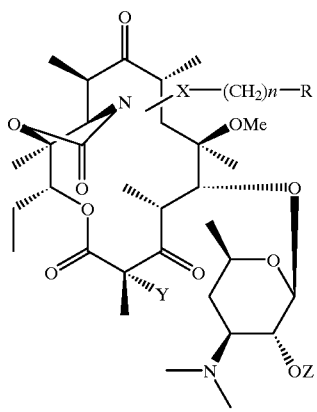

(I)

in which X represents a $CH_2$ or NH radical, n represents an integer comprised between 1 and 8, Y represents a hydrogen or halogen atom, R represents a

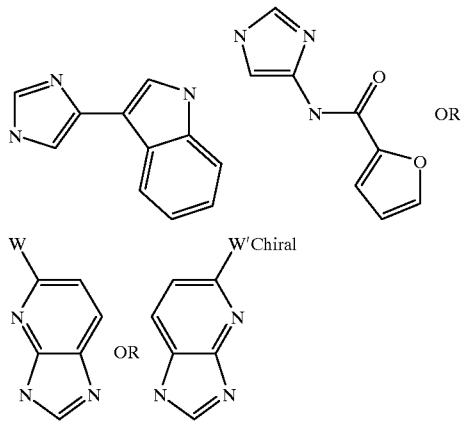

radical, W and W' representing a hydrogen atom, a halogen atom, an alkyl radical containing up to 8 carbon atoms optionally substituted by one or more halogen atoms and Z represents a hydrogen atom or the remainder of an acid as well as their addition salts with acids.

Among the addition salts with acids, there can be mentioned the salts formed with the following acids: acetic, propionic, trifluoroacetic, maleic, tartaric, methanesulphonic, benzenesulphonic, p-toluenesulphonic and especially stearic, ethylsuccinic or laurylsulphonic acids. When Y represents a halogen atom, it is for example, a fluorine, chlorine or bromine atom.

A more particular subject of the invention is the compounds of formula (I) in which X represents a $CH_2$ radical, those in which Y represents a hydrogen atom, those in which Y represents a fluorine atom, those in which n represents the number 4.

A more particular subject of the invention is the compounds the preparation of which is given hereafter in the experimental part, and quite particularly the products of Examples 1, 3 and 5.

The products of general formula (I) have a very good antibiotic activity on gram ⊕ bacteria such as staphylococci, streptococci, pneumococci.

The compounds of the invention can therefore be used as medicaments in the treatment of germ-sensitive infections and in particular, in that of malignant staphylococcia of the face or skin, pyodermitis, septic or suppurating wounds, boils, anthrax, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as pneumonia, bronchitis, brucellosis, diphtheria, gonococcal infection.

The products of the present invention are also active against infections caused by germs such as Haemophilus influenzae, Rickettsia, Mycoplasma pneumoniae, Chlamydia, Legionella, Ureaplasma, Toxoplasma, or germs of the Mycobacterium genus.

Therefore, a subject of the present invention is also the products of formula (I) as defined above, as well as their addition salts with pharmaceutically acceptable mineral or organic acids, as medicaments and, in particular antibiotic medicaments.

A more particular subject of the invention is the products of Examples 1, 3 and 5 and their pharmaceutically acceptable salts, as medicaments and, in particular antibiotic medicaments.

A subject of the invention is also the pharmaceutical compositions containing at least one of the medicaments defined above, as active ingredient.

These compositions can be administered by buccal, rectal, parenteral route, or by local route as a topical application on the skin and mucous membranes, but the preferred administration route is the buccal route.

They can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example, apyrogenic sterile water.

The dose administered is variable according to the affection treated, the patient in question, the administration route and the product considered. It can be, for example, comprised between 50 mg and 300 mg per day by oral route for an adult for the product of Example 1.

A subject of the invention is also a preparation process characterized in that a compound of formula (II):

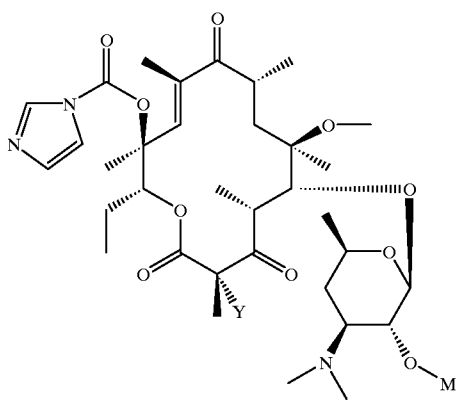

(II)

in which Y retains its previous meaning,

M represents the remainder of an acid is subjected to the action of a compound of formula (III):

R(CH$_2$)nXNH$_2$   (III)

in which R, n and X retain the same meaning as in claim 1 in order to obtain the corresponding compound of formula (I), in which Z represents the remainder of an acid then optionally subjected to the action of an agent which releases the hydroxyl function in position 2' in order to obtain the compound of formula (I) in which Z represents a hydrogen atom and/or subjected to the action of an acid in order to form the salt.

The compounds of formula (II) in which Y represents a hydrogen atom, used as starting products are described and claimed in the European Patent EP 0596802. The products of formula (II) in which Y is a halogen are described and claimed in the European Patent Application 0949268. A detailed example of the preparation of compounds of formula (I) in which Hal represents a fluorine atom is described hereafter. This process can be schematized as follows: compound A,

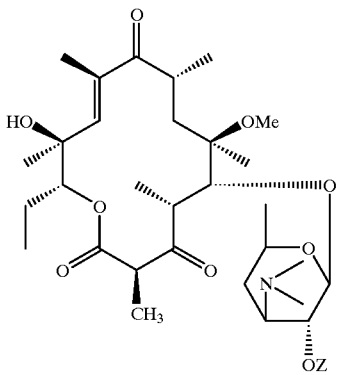

(A)

in which OZ represents a free or protected OH radical, is subjected to the action of a fluorination agent in order to obtain the corresponding compound of formula (B):

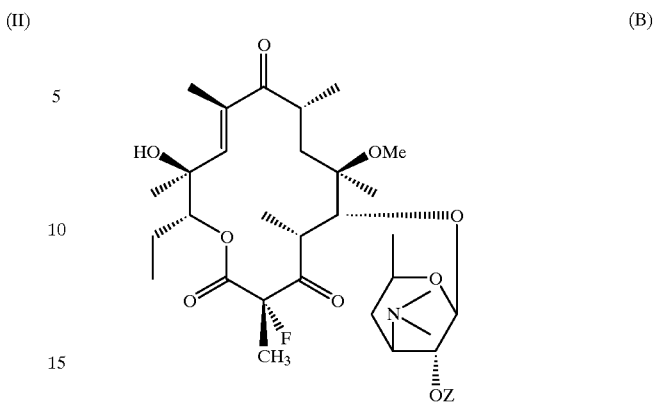

(B)

which is subjected to the action of carbonyldiimidazole, in order to obtain the corresponding compound of formula (II), in which Hal represents a fluorine atom.

The compounds of formula (III) used as starting products are novel and are in themselves a subject of the present invention. Their preparation is given hereafter in the experimental part.

A subject of the invention is also the compounds of formula (III) as defined above, as novel chemical products and especially the compounds of formula (III) in which n represents the number 3 and X represents a CH$_2$ radical.

The following examples illustrate the invention.

EXAMPLE 1

11,12-dideoxy-3-de[(2,6-dideoxy-3-C-methyl-3-O-methyl-.alpha.-L-ribo-hexopyranosyl)oxy]-6-O-methyl-3-oxo-12,11-[oxycarbonyl[[4-[4-(1H-indol-3-yl)-1H-imidazol-1-yl]butyl]-imino]]erythromycin A mixture of 3.78 g of the amin obtained at Preparation 1, 25 ml of acetonitrile, 2.5 ml of water and 4.2 g of 12-(oxycarbonylimidazol)-11-deoxy-10,11-didehydro-3-de[2,6-dideoxy-3C-methyl-3-O-methyl-α-L-ribohexopyranosyl)oxy]6-O-methyl-3-oxo-erythromycin 2'-acetoxy is agitated at 70° C. for 48 hours. After evaporation to dryness, 30 ml of methanol is added and agitation is carried out for 3 hours under reflux. After evaporation to dryness, the product obtained is chromatographed on silica eluting with an ethyl acetate, ethanol, triethylamine mixture 90-5-5. 2.2 g of product is obtained which is purified on silica eluting with a chloroform-methanol-ammonium hydroxide mixture 96-4-0.5. 1.73 g of a product is obtained which is taken up in ethyl acetate, washed with an aqueous solution of ammonium hydroxide at 1%, dried, filtered, evaporated to dryness, followed by impasting in ethyl ether, separating and drying. 1.440 g of sought product is obtained.

NMR spectrum (400 MHz in CDCl$_3$) H2: 3.86 ppm; H4: 3.08 ppm; H5: 4.25 ppm; H7: 1.60 1.81 ppm; H8: 2.60 ppm; H10: 3.13 ppm; H11: 3.58 ppm; H13: 4.95 ppm; H14: 1.56 1.96; H15: 0.83 ppm; 2Me: 1.38 ppm; 4Me: 1.31 ppm; 6Me: 1.34 or 1.47 ppm; 8Me: 1.15 ppm; 10Me: 1.00 ppm; 12Me: 1.34 or 1.47 ppm; 6OMe: 2.65 ppm; 1': 4.29 ppm; 2': 3.19 ppm; 3': 2.45 ppm; 4': 1.66 and 1.23 ppm; 5': 3.53 ppm; NMe$_2$: 2.26 ppm; NCH$_2$: 3.65 3.76 ppm; CH$_2$: 1.68 1.91 ppm; CH$_2$N: 3.99 ppm; imidazole: 7.23 7.53 ppm; indole: 8.60 7.67 7.39 7.18 7.90 ppm.

Mass spectrum MH$^+$: 850$^+$ Desosamine: 158$^+$ M—H$^-$: 848$^-$

EXAMPLE 2

11,12-dideoxy-3-de[(2,6-dideoxy-3-C-methyl-3-O-methyl-.alpha.-L-ribo-hexopyranosyl)oxy]-2-fluoro-6-O-methyl-3- oxo-12,11-[oxycarbonyl[[4-[4-(1H-indol-3-yl)-1H-imidazol-1-yl]-butyl]-imino]]-erythromycin By operating as in Example 1, starting with the 2-fluorinated compound of formula (II), obtained as indicated in preparation 2 given hereafter, the sought product is obtained.

NMR spectrum (400 MHz in CDCl$_3$) H4: 3.53 ppm; H5: 4.07 ppm; H7: 1.52 1.85 ppm; H8: 2.62 ppm; H10: 3.19 ppm; H11: 3.44 ppm; H13: 4.89 ppm; H14: 1.63 1.98; 15Me: 0.87 ppm; 2Me: 1.79 ppm 4Me: 1.32 ppm; 6Me: 1.34 or 1.50 ppm; 8Me: 1.16 ppm; 10Me: 1.01 ppm; 12Me: 1.34 or 1.50 ppm; 6OMe: 2.57 ppm; 1': 4.31 ppm; 2': 3.20 ppm; 3': 2.48 ppm; 4': 1.68 and 1.24 ppm; 5': 3.53 ppm; NMe$_2$: 2.28 ppm; CH$_2$: 1.66 1.86 ppm; CH$_2$N: 3.74 3.69 ppm Mass spectrum MH$^+$: 868$^+$

EXAMPLE 3

11,12-dideoxy-3 de[(2,6-dideoxy-3-C-methyl-3-O-methyl-.alpha.-L-ribo-hexopyranosyl)oxy]-6-O-methyl-3-oxo-12,11-[oxycarbonyl-[[4-[4-[(2-furanylcarbonyl)-amino]-1H-imidazol-1-yl]-butyl]-imino]]-erythromycin By operating as previously the sought product is obtained. rf=0.25 (CH$_2$Cl$_2$ CH$_3$OH NH$_4$OH 95-5-04)

NMR spectrum CDCl$_3$ H2: 3.85 ppm; H4: 3.07 ppm; H5 4.24 ppm; H7: 1.58 and 1.84 ppm; H8: 2.62 ppm; H10: 3.12 ppm; H11: 3.56 ppm; H13: 4.91 ppm; H14: 1.60–1.97 ppm; H15: 0.85 ppm; 2Me: 1.25 ppm; 4Me: 1.30 ppm; 6Me: 1.36 or 1.47 ppm; 8Me: 1.17 ppm; 10Me: 1.00 ppm; 12Me: 1.36 or 1.47 ppm; 6 OMe: 2.63 ppm; 1': 4.28 ppm; 2': 3.20 ppm; 3': 2.48 ppm; 4': 1.67 and 1.23 ppm; 5': 3.56 ppm; 5Me: 1.25 ppm; N(Me)$_2$: 2.28 ppm; NCH$_2$: 3.96 ppm; CH$_2$: 1.84 ppm; CH$_2$: 1.62 ppm; CH$_2$N: 3.63 and 3.32 ppm; H2, H5: 7.39 and 7.28 ppm; H3: 7.18 ppm; H4: 6.53 ppm; H5: 7.50 ppm; NHC=O: 8.30 ppm.

EXAMPLE 4

11,12-dideoxy-3 de[(2,6-dideoxy-3-C-methyl-3-O-methyl-.alpha.-L-ribo-hexopyranosyl)-oxy]-2-fluoro-6-O-methyl-3-oxo-12,11-[oxycarbonyl-[[4-[4-(2-furanylcarbonyl)-amino]-1H-imidazol-1-yl]-butyl]-imino]]-erythromycin By operating as previously the sought product is obtained.

NMR spectrum CDCl$_3$ H4: 3.54 ppm; H5 4.07 ppm; H7: 1.51 and 1.87 ppm; H8: 2.62 ppm; H10: 3.10 ppm; H11: 3.42 ppm; H13: 4.86 ppm; H14: 1.65–1.98 ppm; H15: 0.89 ppm; 2Me: 1.78 (d) ppm; 4Me: 1.31 ppm; 6Me: 1.36 or 1.50 ppm; 8Me: 1.19 ppm; 10Me: 1.01 ppm; 12Me: 1.36 or 1.50 ppm; 6 Ome: 2.55 ppm; 1': 4.31 ppm; 2': 3.20 ppm; 3': 2.48 ppm; 4': 1.69 and 1.24 ppm; 5': 3.54 ppm; 5'Me: 1.24 ppm; N(Me)$_2$: 2.29 ppm; NCH$_2$: 3.58–3,71 ppm; CH$_2$: 1.62 ppm; CH$_2$: 1.83 ppm; CH$_2$N: 3.94 ppm; imidazole: 7.27–7.39 ppm; NH: 8.65 ppm; furan H3: 7.18 ppm; H4: 6.52 ppm; H5: 7.49 ppm.

EXAMPLE 5

11,12-dideoxy-3 de[(2,6-dideoxy-3-C-methyl-3-O-methyl-alpha-L-ribo-hexopyranosyl)-oxy-6-O-methyl-3-oxo-12,11-[oxycarbonyl-[[4-[5-chloro-1H-imidazo[4,5-b]pyridin-1-yl]-butyl]-imino]]-erythromycin 799 g of product of Preparation 3, 5 ml of THF, 5 ml of isopropanol, 706 mg of 12(oxycarbonylimidazol)-11-deoxy-10,11-didehydro-3-de[2,6-dideoxy-3-C-methyl-3-O-methyl-α-L-ribohexopyranosyl) oxy]6-O-methyl-3-oxo-erythromycin 2'acetoxy and 30 µl of DBU are agitated for 48 hours at ambient temperature. The reaction medium is poured into water, extracted with ethyl acetate, washed with water, dried, filtered and concentrated. The product obtained is poured into 7 ml of methanol and agitated for 24 hours at ambient temperature, followed by concentration under reduced pressure. The product obtained is purified by chromatography on silica eluting with a methylene chloride, methanol, ammonium hydroxide mixture 95-5-0.3. 240 mg of a product is isolated which is solubilized in ethyl acetate, washed with ammonium hydroxide, dried, filtered and brought to dryness. The product obtained is crystallized from ethyl ether, washed and dried under reduced pressure at 70° C. 117 mg of sought product is isolated M.p.= 200~202° C. MS: MH$^+$=820$^+$. NMR CDCl$_3$ ppm 3.86: H2; 3.06: H4; 4.24: H5; 2.60: H8; 3.14: H10; 3.54: H11; 4.88: H13; 1.38: 2Me; 1.30: 4Me; 1.16: 8Me; 100: 10-Me; 2.59: 6OMe; 4.27: H1'; 3.17: H2'; 2.45: H3'; 3.54: H5'; 1.25: 5'Me; N(Me)$_2$: 2.26; NCH$_2$: 3.64–3.80; CH$_2$N: 4.24; H2: 8.14; H6, H7: 7.28–7.78.

EXAMPLE 6

11,12-dideoxy-3 de[(2,6-dideoxy-3-C-methyl-3-O-methyl-.alpha.-L-ribo-hexopyranosyl)-oxy]-6-O-methyl-3-oxo-12,11-[oxycarbonyl-[[4-[5-chloro-3H-imidazo[4,5-b]pyridin-3-yl]-butyl]-imino]]-erythromycin By operating as previously the sought product is obtained. MS: MH$^+$=820$^+$.

NMR: CDCl$_3$ 400Mhe H2: 3.84(q); H4: 3.06(m); H5: 4.24(d); H8: 2.60(masked); H10: 3.13(q); H11: 3.55(s); H13: 4.91(dd); H15 : 0.85(t); 2Me: 1.37(d); 4Me: 1.30(d); 8Me: 1.16(d); 10Me: 1.00(d); 12Me: 1.36 or 1.46(s); 6OMe: 2.60(s); H1': 4.29(d); H2': 3.18(dd); H3': 2.45(m); H4': 1,24–1,68(m); H5': 3.55(m); 5'Me: 1.26(d); N(Me): 2.26(s); O—CO—N—CH$_2$: 3.67–3.75(m); CH$_2$: 1.68(m) CH$_2$: 1.96 (m); NCH$_2$: 4.33(m); H2": 8.09(s); H4": 7.98(d); H5": 7.22(d).

Preparation 1
4-(1H-indol-3-yl)-1H-imidazole-1-butanamine
Stage A
3-(1H-imidazole-4-yl)-1H-indole 12.87 g of 2-bromo-1-(1H-indol-3-yl)-ethanone and 27.4 ml of formamide are agitated for one hour at 180° C., followed by taking up in water, washing with ethyl acetate, adjusting to a pH greater than 10 with a 5% solution of ammonium hydroxide, extracting with ethyl acetate, drying and evaporating to dryness. The product obtained is chromatographed on silica eluting with a methylene chloride-methanol-ammonium hydroxide mixture 96-4-0.5, 2.53 g of sought product is obtained.
Stage B
2-[4-[4-(1H-indol-3-yl)1H-imidazol-1-yl]butyl]-1H-isoindole-1,3(2H)-dione 7.9 g of product of Stage A, 50 ml of DMF and 11.93 g of potassium carbonate are agitated for 15 minutes at 110° C., dried in an oven under phosphoric anhydride. A solution of 15.83 g of N-(4-bromobutyl)phthalimide in 30 ml of DMF is added dropwise at ambient temperature. Agitation is carried out for one hour at 110° C. The reaction medium is poured into sodium acid phosphate, followed by evaporation under reduced pressure. 19.11 g of crude product is obtained which is purified on silica eluting with a methylene chloride-methanol-ammonium hydroxide mixture 97-3-05. 4.58 g of sought product is obtained.
Stage C
4-(1H-indol-3-yl)-1H-imidazole-1-butanamine A mixture of 4.58 g of product of the preceding stage, 200 ml of ethanol and 1.45 ml of hydrazine hydrate is agitated for 24 hours under reflux, followed by concentrating to 30 ml, filtering, rinsing with ethanol and evaporating to dryness. 3.78 g of sought product is obtained.
Preparation 2: 12-(oxycarbonyl-imidazol)-11-deoxy-10,11-didehydro-3-de[2,6-dideoxy-3-C-methyl-3-O-methyl-α-L- ribohexopyranosyl)-oxy]-6-O-methyl-3-oxo-erythromycin 2'-acetoxy 2α-fluoro

Stage A 11-deoxy-10,11-didehydro-3-de[(2,6-dideoxy-3-C-methyl-3-O-methyl-α-L-ribonhexopyranosyl)oxy]-6-O-methyl-3-oxo-erythromycin A mixture of 8.22 g of 2'-acetoxy-11-deoxy-10,11-didehydro-3-de[(2,6-dideoxy-3-C-methyl-3-O-Methyl-α-L-ribohexo-pyranosyl)-oxy]-6-O-Methyl-3-oxo-erythromycin (EP 596802) and 350 ml of anhydrous methanol is agitated for 44 hours, followed by evaporating, taking up in methylene chloride, drying and 8.794 g of sought product is obtained.

Stage B 11-deoxy-10,11-didehydro-3-de[(2,6-dideoxy-3-C-methyl-3-O-methyl-α-L-ribohexopyranosyl)oxy]-6-O-methyl-3-oxo-erythromycin 2'-trimethylsilyloxy A mixture containing 3.08 g of the product of the preceding stage, 340 mg of imidazole, 32 ml of anhydrous THF and 1.06 ml of hexamethyl-disilylazane is agitated at ambient temperature for 4 days. The reaction medium is evaporated to dryness, taken up in a mixture of 60 ml of methylene chloride and 60 ml of a 0.5 M aqueous solution of sodium acid phosphate. The mixture is maintained under agitation for 15 minutes, decanted, extracted with methylene chloride, dried and evaporated to dryness. 3.345 g of the sought product is obtained.

Stage C 11-deoxy-10,11-didehydro-3-de[(2,6-dideoxy-3-O-methyl-α-L-ribohexo pyranosyl) oxy]-6-O-methyl-3-oxo-erythromycin 2'-trimethylsilyloxy-2α-fluoro 1.24 ml of a solution of potassium terbutylate in 0.97 M THF is added at −12° C. under an argon atmosphere to a solution containing 668 mg of 11-deoxy-10,11-didehydro-3-de[(2,6-dideoxy-3-O-methyl-α-L-ribohexopyranosyl) oxy]-6-O-methyl-3-oxo-erythromycin 2'-trimethylsilyloxy and 6.7 ml of anhydrous THF. The reaction medium is agitated for 5 minutes and 378 mg of N-fluoro dibenzene-sulphonimide is added. The reaction medium is agitated for 10 minutes at −12° C. and left to return to ambient temperature over 1 hour 30 minutes. Isolation and purification operations are carried out and 695 mg of the sought product is obtained.

Stage D 11-deoxy-10,11-didehydro-3-de[(2,6-dideoxy-3-C-methyl-3-O-methyl-α-L-ribohexopyranosyl)oxy]-6-O-methyl-3-oxo-erythromycin 2α-fluoro A mixture of 5.476 g of the product of the preceding stage, 50 ml of THF and 11.2 ml of 1M tetrabutylammonium fluoride in THF is agitated for 3 hours 30 minutes. The solvent is evaporated off and 37 ml of ethyl acetate, 37 ml of water and 7.5 ml of 20% ammonium hydroxide are added. Agitation is carried out for 10 minutes, followed by decanting, extracting with ethyl acetate, drying, filtering and the filtrate is concentrated to dryness. The product obtained is chromatographed on silica eluting with an ammoniated $CH_2Cl_2$-MeOH mixture 99-1, then 98-2, 97-3, 96-4, 95-5. 2.452 g of sought product is obtained.

Stage E 11-deoxy-10,11-didehydro-3-de[(2,6-dideoxy-3-O-methyl-α-L-ribohexopyranosyl)oxy]-6-O-methyl-3-oxo-erythromycin 2'-acetoxy-2α-fluoro 1.02 g of the product of Stage A, 10 ml of methylene chloride and 241 μl of acetic anhydride are maintained under agitation for 3 hours, followed by evaporation and 10 ml of water and 10 ml of ethyl acetate are added. The reaction medium is left under agitation for 1 hour at ambient temperature, decanted, dried and evaporated. 1.01 g of sought product is obtained.

Stage F 12-(oxycarbonylimidazol)-11-deoxy-10,11-didehydro-3-de[(2,6-dideoxy-3-C-methyl-3-O-methyl-α-L-ribohexopyranosyl)oxy]-6-O-methyl-3-oxo-erythromycin 2'-acetoxy-2α-fluoro 0.388 g of carbonyldiimidazole and 24 μl of DBU are added at 0° C. to a solution containing 1.01 g of the product of the preceding stage and 10 ml of anhydrous THF. The reaction mixture is maintained under agitation at 0° C. for 19 hours. The THF is evaporated off and 10 ml of water and 10 ml of ethyl acetate are added. The reaction mixture is maintained under agitation for 10 minutes, extracted, dried and evaporated. 0.902 g of crude sought product is obtained which is chromatographed eluting with an ethyl acetate-triethylamine mixture 96-4. 0.573 g of sought product is obtained.

Preparation 3

N-[1-(4-aminobutyl)-1H-imidazol-4-yl]-2-furancarboxamide

Stage A

2-[4-(4-nitro-1H-imidazol-1-yl)butyl]-1H-isoindole-1,3 (2H)dione

A mixture of 15 g of 4-nitro-1H-imidazole, 250 ml of DMF, 26.95 g of potassium carbonate and 37.41 g of 2-(4-bromobutyl)-1H-isoindole-1,3(2H dione) are taken to reflux for 2 hours. The reaction medium is left to return to ambient temperature and poured into water. After filtering, rinsing and drying, 33.31 g of sought product is obtained.

Stage B 4-nitro-1H-imidazole-1-butanamine

A mixture of 33.31 g of the product of Stage A, 555 ml of ethanol and 11.33 ml of hydrazine are taken to reflux for 20 hours. After filtering, the reaction medium is left to return to ambient temperature and brought to dryness. 33.04 g of product is obtained.

Stage C 1,1-dimethylethyl [4-(4-nitro-1H-imidazol-1-yl)butyl]-carbamate 33.04 g of the product of the preceding stage, 665.8 ml of THF, 222.32 ml of water, 19.2 ml of triethlylamine, and 27.76 g of terbutylic anhydride are agitated for 1 hour 30 minutes at ambient temperature. The reaction medium is concentrated under reduced pressure and taken up in water, followed by separating, washing and drying under reduced pressure at 60° C. 20.3 g of sought product is obtained.

Stage D 1,1-dimetylethyl [4-(4-amino-1H-imidazol-1-yl)butyl]-carbamate

A mixture of 19.25 g of the product of the preceding stage, 5.77 ml of ethanol and 19 g of Raney nickel is hydrogenated. After filtering and rinsing with ethanol under a nitrogen atmosphere 21.38 g of sought product is obtained.

Stage E 1,1-dimethylethyl[4-[4-[(2-furanylcarbonyl)amino-1H-imidazol-1-yl)butyl]-carbamate A mixture of 21.38 g of product of the preceding stage, 962 ml of THF and 14.19 ml of triethylamine is agitated for 5 minutes under a nitrogen atmosphere. The reaction medium is taken to 0° C. and 7.52 ml of 2-furanyl carbonyl chloride is introduced. The reaction medium is left to return to ambient temperature, agitated for 2 hours eluting a with methylene chloride-methanol mixture 96-4, followed by pouring into water. Agitation is carried out and 500 ml of ethyl acetate is added, followed by agitating, decanting and extracting with ethyl acetate. The organic phase is washed with water, dried, filtered and brought to dryness. 25.18 g of sought product is obtained.

Stage F
N-[1-(4-aminobutyl)-1H-imidazol-4-yl]-2-furan-carboxamide

A solution of 25.18 g of the product of the preceding stage and 126 ml of methylene chloride is taken to 0° C. 103 ml of TFA is added dropwise. The reaction medium is left to return to ambient temperature and agitated for 1 hour 30 minutes. The methylene chloride is evaporated off, followed by taking up in ether, agitating for 1 hour in the presence of ether, filtering and drying. A product is obtained which is purified on resin. 9.4 g of sought product is obtained.

Preparation 4

5-chloro-3H-imidazo [4,5-b]pyridine-3-butanamine and 5-chloro-1H-imidazo[4,5-b]pyridine-1-butanamine Stage A
6-chloro 2,3-pyridindiamine 4.484 g of iron powder is added to a solution containing 78 ml of acetic acid and 3.415 g of 6-chloro-3-nitro-2-pyridinamine. The reaction medium is heated at 60° C.–70° C. for 2 hours 45 minutes, then left to return to ambient temperature. After pouring into 200 ml of water, 200 ml of ammonium hydroxide is added until pH9 is achieved, followed by extraction with ethyl acetate, drying, filtering and concentrating. 3.14 g of crude product is obtained which is chromatographed on silica eluting with an ethyl acetate triethylamine mixture 95/5. 2.43 g of sought product is obtained.

Stage B
5-chloro-1H-imidazo[4,5-b]pyridine

A solution containing 5.16 g of the product of the preceding stage and 50 ml of formic acid is taken to reflux for 16 hours. The product obtained is impasted in ethyl ether and separated. The product obtained is put into 60 ml of a 2N aqueous solution of soda. The aqueous phase is extracted with an ethyl acetate tetrahydrofuran mixture 80–20 and washed with salt water. The organic phases are combined, dried over anhydrous sodium sulphate, filtered and brought to dryness. In this way 2 g of sought product is isolated M.p.=226~280° C. 0.79 g of sought product is obtained from the mother liquors M.p.=225~27° C.

Stage C
2-[4-5-chloro-3H-imidazo[4,5-b]pyridine-3-yl]butyl]-1H-isoindole-1,3(2H)-dione 461 mg of the product of the preceding stage and 5 ml of DMF on siliporite are poured into a suspension containing 2.5 ml of DMF and 173 mg of sodium hydride at 50% in oil. The reaction medium is heated to 60° C. for 10 minutes. 864 mg of N-(4-bromobutylphthalimide) and 5 ml of DMF are poured in. Agitation is carried out for 2 hours 30 minutes at ambient temperature, followed by pouring into a mixture of ice, water and ethyl acetate. Extraction is carried out with ethyl acetate followed by washing with water. The aqueous phases are combined, dried, filtered and concentrated. 1.58 g of the product is isolated which is chromatographed on silica and 583 mg of isomer A product is obtained M.p.= 137~139° C.

NMR spectrum: CDCl$_3$, 250 MH$_2$ 1.77(m)2H central 2CH$_2$'s; 1.98(m)2H central 2CH$_2$'s; 3.76(t) 2H CH$_2$—CH$_2$-Pht; 4.34(t) 2H=C—N—CH$_2$—CH$_2$; 7.23(d, J=8)H$_6$; 8.00 (d, J=8)H7; 8.06(s)H2; 7.72(m)2H phthalimide; 7.84(m)2H Phthalamide MS: 355$^+$: MH$^+$ 418$^+$: MNa$^+$+CH$_3$CN 731$^+$: 2M$^+$+Na
The 2$^{nd}$ isomer B is isolated M.p.=181–182° C.

NMR Spectrum: CDCl$_3$ 1.75(m) 1.93(m) central 2CH$_2$'s; 3.75(t) CH$_2$CH$_2$Pht; 4.28(t)

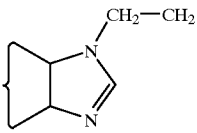

7.25(d, J=8.5)H6; 7.74(d, J=8.5)H7; 7.74(m) 7.85(m) 4H phthalimide; 8.13(s)H2

NMR Spectrum: DMSO 1.55(m) 1.83(m) central 2CH$_2$'s; 3.60(t)CH$_2$CH$_2$-Pht; 4.32(t) C—N—CH$_2$—CH$_2$; 7.33(d, J=8.5)H6; 8.20(d, J=8,5)H7; 8.55(d)H2; 7.84(m) 4H Phthalimide Stage D
5-chloro-3H-imidazo[4,5-b]pyridine-3-butanamine A suspension containing 10 ml of ethanol, 0.815 g of the product of the preceding stage (isomer A) and 225 µl of hydrazine hydrate is taken to reflux. The reaction medium is heated under reflux for 18 hours, left to return to ambient temperature, then filtered, rinsed with ethanol and brought to dryness. 799 mg of sought product is obtained.

Stage E
5-chloro-1H-imidazo[4,5-b]pyridine-1-butanamine

By operating as in Stage D starting with 355 mg of the product of Stage C (isomer B), 146 mg of the sought product was obtained.

NMR spectrum CDCl$_3$ 300 MH$_2$ 1.52 and 1.99 the central CH$_2$'s; 2.20 NH2; 2.77(t) CH$_2$NH$_2$; 4.30(t)CH$_2$NC; 7.25(d) H6; 8.00(d) H7; 8.06(s)H2

MS: 225$^+$: MH$^+$ 266$^+$: MH$^+$+CH$_3$CN 154$^+$: [MH$^+$ (CH$_2$)$_4$—NH$_2$)]$^+$

EXAMPLE OF PHARMACEUTICAL COMPOSITION

Tablets were prepared containing:

| | |
|---|---|
| Product of example 1 | 150 mg |
| Excipient s.q.f | 1 g |

Detail of excipient: starch, talc, magnesium stearate

PHARMACOLOGICAL STUDY OF THE PRODUCTS OF THE INVENTION

Method of dilutions in liquid medium

A series of tubes is prepared in which the same quantity of nutritive sterile medium is distributed. Increasing quantities of the product to be studied are distributed into each tube, then each tube is sown with a bacterial strain. After incubation for twenty-four hours in a heating chamber at 37° C., the growth inhibition is evaluated by transillumination, which allows the minimal inhibitory concentrations (M.I.C.) to be determined, expressed in micrograms/cm$^3$.

The following results were obtained: (reading after 24 hours)

| | | PRODUCT OF EXAMPLE: | | |
|---|---|---|---|---|
| No | | 1 | 3 | 5 |
| 01 S. aureus | 011UC4 | 0.040 | 0.150 | 0.02 |
| 02 S. aureus | 011UC4 + | 0.040 | 0.150 | 0.600 |

-continued

| No | | PRODUCT OF EXAMPLE: | | |
|---|---|---|---|---|
| | | 1 | 3 | 5 |
| | | serum 50% | | |
| 03 | S. aureus | 011B18c | | |
| 04 | S. aureus | 011GR12c | | |
| 05 | S. aureus | 041GO25i | 0.080 | 0.150 | 0.040 |
| 06 | S. epidermidis | 012GO11i | 0.080 | 0.40 | 0.150 |
| 07 | S. aureus | 011CB20c | | |
| 08 | S. epidermidis | 012GO40c | | |
| 09 | S. pyogenes | 02A1UC1 | 0.02 | 0.150 | 0.080 |
| 10 | S. agalactiae | 02B1HT1 | 0.02 | 0.02 | 0.02 |
| 11 | S. faecalis | 02D2UC1 | 0.040 | 0.040 | 0.02 |
| 12 | S. faecium | 02D3HT1 | 0.02 | 0.040 | 0.02 |
| 13 | Streptococcus gr. G | 02GOGR5 | 0.040 | 0.040 | 0.02 |
| 14 | S. mitis | 62MitCB1 | 0.02 | 0.040 | 0.02 |
| 15 | S. pyogenes | 02A1SJ1c | 5.000 | 10.000 | 10.000 |
| 16 | S. agalactiae | 02B1SJ1c | 0.080 | 0.040 | 0.080 |
| 17 | S. faecalis | 02D2DU15c | 10.000 | 2.500 | 10.000 |
| 18 | Streptococcus gr. G | 02GOgr4c | 20.000 | 10.000 | 20.000 |
| 19 | S. sanguis | 02SgGr10i | 0.150 | 0.040 | 0.080 |
| 20 | S. mitis | 02MitGR16i | 0.02 | 0.02 | 0.040 |
| 21 | S. pneumoniae | 032UC1 | 0.02 | 0.080 | 0.02 |
| 22 | S. pneumoniae | 030GR20 | 0.02 | 0.02 | 0.02 |
| 23 | S. pneumoniae | 030SJ5i | 0.040 | 0.02 | 0.080 |
| 24 | S. pneumoniae | 030CR18c | 0.600 | 0.300 | 2.500 |
| 25 | S. pneumoniae | 030PW23C | 0.080 | 0.040 | 0.02 |
| 26 | S. pneumoniae | 030RO1i | 0.080 | 0.080 | 0.040 |
| 27 | S. pneumoniae | 030SJ1C | 0.080 | 0.080 | 0.0300 |

What we claim is:

1. A compound selected from the group consisting of a compound of the formula

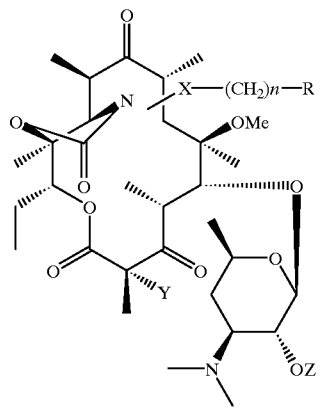

I wherein X is —$CH_2$ or —NH—, n represents an integer from 1 to 8, Y is hydrogen or halogen, R is selected from the group consisting of

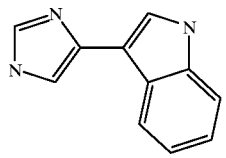

and

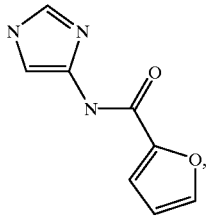

Z is hydrogen or acyl of an organic carboxylic acid of 1 to 6 carbon atoms and its non-toxic, pharmaceutically acceptable acid addition salts.

2. A compound of claim 1 wherein X is —$CH_2$—.
3. A compound of claim 1 wherein Y is hydrogen.
4. A compound of claim 1 wherein Y is fluorine.
5. A compound of claim 1 wherein n is 4.
6. A compound of claim 1 selected from the group consisting of 11,12-dideoxy-3-de-[(2,6-dideoxy-3-C-methyl-3-0-methyl-α-L-ribohexopyranosyl)oxy]-6-0-methyl-3-oxo-12,11-[oxycarbonyl[[4-[4-(1H-indol-3-yl)-1H-imidazol-1-yl]-butyl]-imino]]-erythromycin and 11,12-dideoxy-3-de-[(2,6-dideoxy-3-C-methyl-3-0-methyl-α-L-ribohexopyranosyl)oxy]-6-0-methyl-3-oxo-12,11-[oxycarbonyl[[4-[4-[(2-furanylcarbonyl)amino]-1H-imidazol-1-yl]-butyl]-imino]]-erythromycin.
7. An antibiotic composition comprising an antibiotically effective amount of a compound of claim 1 and an inert pharmaceutical carrier.
8. A method of treating bacterial infections in warm-blooded animals comprising administering to the warm blooded animals a bactericidally effective amount of a compound of claim 1.
9. The method of claim 8 wherein X is —$CH_2$—.
10. The method of claim 8 wherein Y is hydrogen.
11. The method of claim 8 wherein Y is fluorine.
12. The method of claim 8 wherein n is 4.
13. A method of claim 8 wherein the compound is selected from the group consisting of 11,12-dideoxy-3-de-[(2,6-dideoxy-3-C-methyl-3-0-methyl-α-L-ribohexopyranosyl)oxy]-6-0-methyl-3-oxo-12,11-[oxycarbonyl[[4-[4-(1H-indol-3-yl)-1H-imidazol-1-yl]-butyl]-imino]]-erythromycin and 11,12-dideoxy-3-de-[(2,6-dideoxy-3-C-methyl-3-0-methyl-α-L-ribohexopyranosyl)oxy]-6-0-methyl-3-oxo-12,11-[oxycarbonyl[[4-[4-[(2-furanylcarbonyl)amino]-1H-imidazol-1-yl]-butyl]-imino]]-erythromycin.
14. A process for the preparation of a compound of claim 1 comprising reacting a compound of the formula

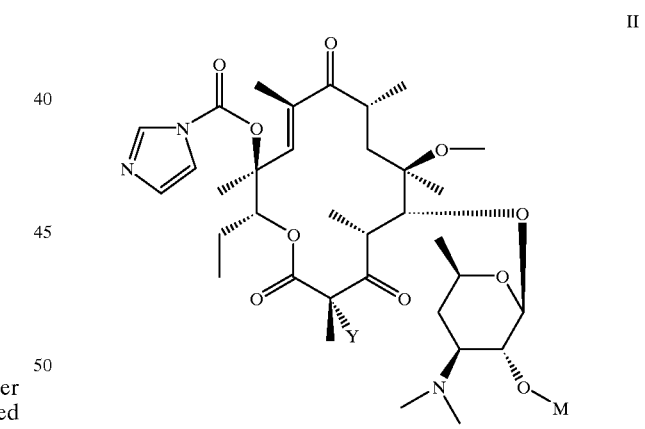

II wherein y is hydrogen or halogen and M is an acyl of an organic carboxylic acid of 1 to 6 carbon atoms with a compound of the formula

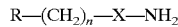

R—$(CH_2)_n$—X—$NH_2$      III wherein R, n and X are defined as in claim 1 to obtain the compound of claim 1 wherein Z is acyl of an organic carboxylic acid of 1 to 6 carbon atoms and optionally hydrolyzing the latter compound to obtain a compound of claim 1 wherein Z is hydrogen.

* * * * *